United States Patent
Berger et al.

(10) Patent No.: US 10,663,452 B2
(45) Date of Patent: May 26, 2020

(54) DATA MANAGEMENT UNIT FOR SUPPORTING HEALTH CONTROL

(71) Applicant: Sanofi-Aventis Deutschland GMBH, Frankfurt am Main (DE)

(72) Inventors: Lars Berger, Frankfurt am Main (DE); Anton Petkov, Frankfurt am Main (DE); Frank Flacke, Frankfurt am Main (DE); Jochen Sieber, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 425 days.

(21) Appl. No.: 15/023,026

(22) PCT Filed: Sep. 19, 2014

(86) PCT No.: PCT/EP2014/070004
§ 371 (c)(1),
(2) Date: Mar. 18, 2016

(87) PCT Pub. No.: WO2015/040166
PCT Pub. Date: Mar. 26, 2015

(65) Prior Publication Data
US 2016/0224756 A1    Aug. 4, 2016

(30) Foreign Application Priority Data

Sep. 20, 2013 (EP) .................................... 13185396

(51) Int. Cl.
| | | |
|---|---|---|
| G01N 33/48 | (2006.01) | |
| G01N 33/50 | (2006.01) | |
| G01N 33/487 | (2006.01) | |
| G16H 40/63 | (2018.01) | |
| G16H 50/50 | (2018.01) | |
| G16H 50/20 | (2018.01) | |
| G01N 27/416 | (2006.01) | |
| G16H 20/10 | (2018.01) | |

(52) U.S. Cl.
CPC ... *G01N 33/48792* (2013.01); *G01N 27/4166* (2013.01); *G16H 40/63* (2018.01); *G16H 50/20* (2018.01); *G16H 50/50* (2018.01); *G16H 20/10* (2018.01)

(58) Field of Classification Search
None
See application file for complete search history.

(56) References Cited

U.S. PATENT DOCUMENTS 7,853,455 B2    12/2010   Brown
7,904,310 B2     3/2011   Brown 2004/0059201 A1*  3/2004  Ginsberg ........... A61B 5/14532
                                                    600/300
2008/0234992 A1   9/2008  Pinaki et al.
2008/0255707 A1  10/2008  Hebblewhite et al.
(Continued)

FOREIGN PATENT DOCUMENTS

EP    2031534    3/2009
EP    2259057   12/2010
(Continued)

OTHER PUBLICATIONS

International Preliminary Report on Patentability in International Application No. PCT/EP2014/070004, dated Mar. 22, 2016, 7 pages.
(Continued)

*Primary Examiner* — Russell S Negin
(74) *Attorney, Agent, or Firm* — Fish & Richardson P.C.

(57) ABSTRACT

The present invention refers to a data management unit for supporting health control and a corresponding medical device comprising a data storage (130) adapted to store a plurality of measurement values of a physiological parameter, for example the fasting blood glucose level, and for each measurement value an associated time stamp and a trend indicator (164), wherein the trend indicator is adapted to indicate different trend categories, for example an increasing trend, a steady trend and a decreasing trend, preferably as a respective visible sign (201,202) on a display (162) and/or as a respective audible signal by a loudspeaker, a processor (140) adapted to select a first group of measurement values and a second group of measurement values from the plurality of measurement values of the data storage (130) such that the associated time stamp of each of the measurement values of the first group is in a predefined first time interval and the associated time stamp of each of the measurement values of the second group is in a predefined second time interval, wherein the second time interval is more recent than the first time interval, wherein the processor is further adapted to calculate a first mean value as a median from the first group of measurement values and a second mean value from the second group of measurement values, wherein the processor (140) interacts with the trend indicator (164) such that the trend indicator (164) indicate one of the different trend categories, for example the increasing trend, the steady trend or the decreasing trend, dependent on a result of a comparison of the second mean value to the first mean value. Additionally, the invention refers to a corresponding method and a computer program for indicating a trend, and to a corresponding computer program product.

24 Claims, 7 Drawing Sheets

(56) References Cited

U.S. PATENT DOCUMENTS

Figure 1:
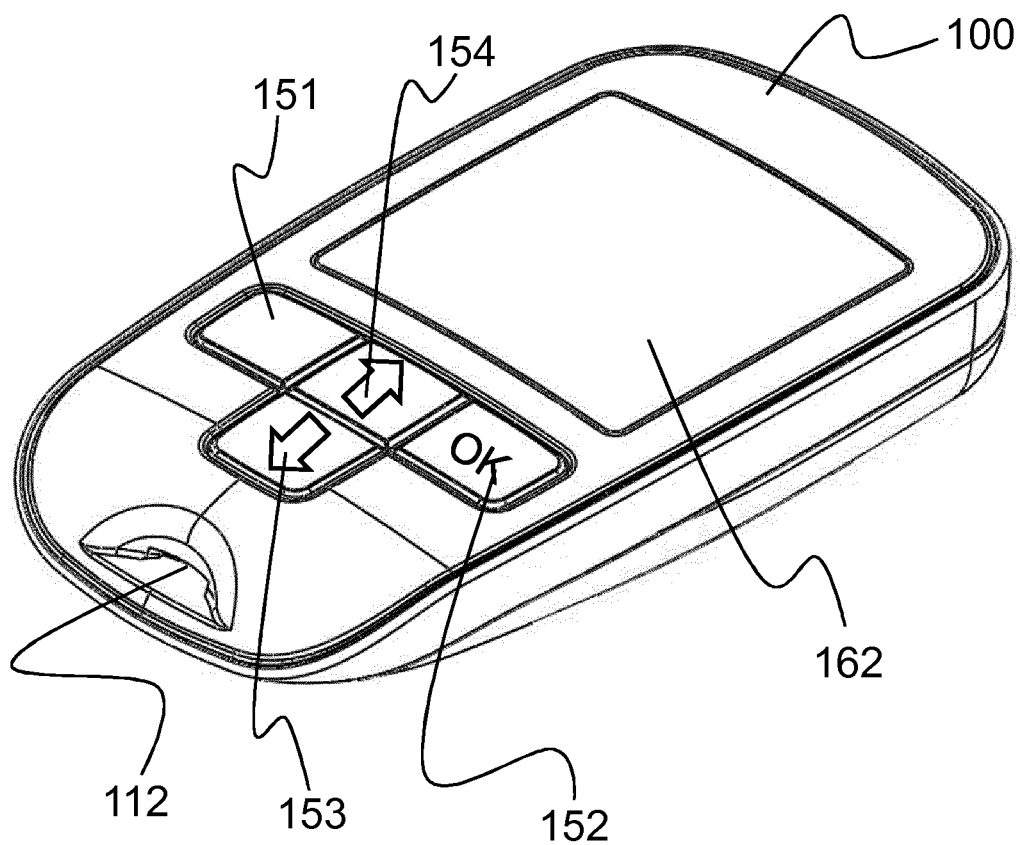

| 2011/0184752 A1* | 7/2011 | Ray | G16H 15/00 705/2 |
| --- | --- | --- | --- |
| 2011/0257496 A1 | 10/2011 | Terashima et al. | |
| 2012/0266251 A1 | 10/2012 | Birtwhistle et al. | |
| 2014/0046160 A1 | 2/2014 | Terashima et al. | |

FOREIGN PATENT DOCUMENTS

| EP | 2486851 | 8/2012 |
| --- | --- | --- |
| EP | 2256495 | 12/2012 |
| JP | S59-69059 | 4/1984 |
| JP | 2007-535974 | 12/2007 |
| JP | 2008-511345 | 4/2008 |
| JP | 2010-75354 | 4/2010 |
| JP | 2010-82009 | 4/2010 |
| JP | 2011-147784 | 8/2011 |
| JP | 2012-196508 | 10/2012 |
| JP | 2012-210366 | 11/2012 |
| WO | WO03/057027 | 7/2003 |
| WO | WO 2005/093629 | 10/2005 |
| WO | WO 2006/021051 | 3/2006 |
| WO | WO2010/149392 | 12/2010 |
| WO | WO2011/007051 | 1/2011 |

OTHER PUBLICATIONS

International Search Report and Written Opinion in International Application No. PCT/EP2014/070004, dated Oct. 14, 2014, 10 pages.

Ratner et al, "Less hypoglycemia with insulin glargine in intensive insulin therapy for type 1 diabetes. U.S. Study Group of Insulin Glargine in Type 1 Diabetes", Diabetes Care, vol. 23, No. 5, May 1, 2000, pp. 639-643.

Rote Liste, "50. Hypophysen-, Hypothalamushormone, andere regulatorische Peptide u. ihre Hemmstoffe," Chapter 50, ed. 2008, 20 pages.

Rodbard, "Optimizing display, analysis, interpretation, and utility of self-monitoring blood glucose (SMBG) data for management of patients with diabetes," Journal of Diabetes Science and Technology 1(1):62-71, Jan. 1, 2007.

* cited by examiner

DATA MANAGEMENT UNIT FOR SUPPORTING HEALTH CONTROL

CROSS-REFERENCE TO RELATED APPLICATIONS

This application is a U.S. national stage application under 35 USC § 371 of International Application No. PCT/EP2014/070004, filed on Sep. 19, 2014, which claims priority to European Patent Application No. 13185396.2, filed on Sep. 20, 2013, the entire contents of which are incorporated herein by reference.

The present invention relates to a data management unit for supporting health control, a method and a computer program for indicating a trend within a plurality of measurement values of a physiological parameter, a respective computer program product, and a medical device for supporting health control.

The following description of the invention mainly refers to diabetes as a health problem and the blood glucose level as the physiological parameter to be controlled in order to assess the effectiveness of the prescribed treatment. However, the invention may also be used with regard to other health problems and for management of other physiological parameter data like (a) blood pressure in hypertensive heart disease, (b) cholesterol or lipoprotein profile in patients with risk factors for heart disease and stroke, (c) peak flow in asthmatic patients, or (d) coagulation in patients treated for hemophilia.

Diabetes mellitus is a group of metabolic diseases in which a person has high blood sugar, either because the pancreas does not produce enough insulin, or because cells do not respond to the insulin that is produced. The treatment of diabetes concentrates on keeping blood sugar levels as close to normal ("euglycemia") as possible, without causing hypoglycemia. This can usually be accomplished with diet, exercise, and use of appropriate medications (insulin in the case of type 1 diabetes; oral medications, as well as possibly insulin, in type 2 diabetes).

Essential elements of the management of diabetes with insulin are periodic checks of the glucose concentration in the blood performed by the patients themselves, in order to obtain regular information on the progress and success of the prescribed treatment. This understanding, and patient participation is vital, since the complications of diabetes are far less common and less severe in people who have well-managed blood sugar levels. With regard to this it has to be considered that the blood glucose level fluctuates throughout the day and is directly influenced by the amount of insulin administered, as well as lifestyle factors such as the amount and kind of food that is consumed, the exercise level and stress.

Therefore, the monitoring of the sugar level in the blood serves a dual purpose: on the one hand it provides the patient with information about the current status of glycemic control. On the other hand can the measured values serve as information for the patient or a healthcare professional (HCP) to determine whether an adjustment in the medication, namely the amount of insulin to be taken, is indicated.

In order to achieve these goals or to get as close as possible to the desired glycemic control, it is common practice that blood glucose measurement (BGM) values are monitored once or several times during the day, following a testing regime normally prescribed by an HCP.

A special role is played by the so-called fasting blood glucose measurement value (FBG). A fasting blood glucose value is derived after several hours without eating (6 to 8 hours). The fasting blood glucose measurement value is typically taken in the morning before breakfast and is the most commonly performed test among insulin treated patients as it is used to assess the quality of the titration of long-acting basal insulin or analogs such as insulin glargine.

In order to adjust or to adapt the therapy it is helpful to record the results of all blood glucose measurements and to analyze these results with a data management unit. Therefore, typically a portable monitor is used which may be able to measure the blood glucose level as well or which receives the measurement values from a blood glucose measurement device. A wireless or wired data transfer can be used to transport the results from the measurement device to the data management unit.

The paper R. E. RATNER et al. "Less hypoglycemia with insulin glargine in intensive insulin therapy for type 1 diabetes . . . ", Diabetes Care vol. 23, no. 5, p. 639 et seqq., 2000 describes a study in which subjects were randomized to receive premeal regular insulin and either insulin glargine or NPH insulin for up to 28 weeks. The efficacy of the therapy was measured including mean changes from baseline of GHb (HbA1c) and capillary FBG levels, median change from baseline of FPG levels, incidence of hypoglycemia, and incidence of hypglcemia with a blood glucose level of <2.0 mmol/L (36 mg/dl). Further, statistics methods were applied for the analysis of the study data. In particular, changes in capillary FBG values from baseline to end point were assessed in the study by using the well known statistics method analysis of covariance (ANCOVA).

Data management units of prior art, in particular for home or medical practice use, usually store the measurement values and are typically able to show graphical representation of data and statistical measures such as average values, which are often difficult for a user to interpret and not or not very suitable to make decisions on the improvement of the treatment. The existing data displays typically require an experienced user and further analysis of the results, which is time consuming.

Further it is observed that a single self-monitoring blood glucose measurement value may be interpreted differently if it is seen in context of previous measurement values of the same time range. Common devices of prior art allow the individual test result to be associated by the user with a tag, intended to indicate a result taken as before or after a meal. Especially for morning fasting readings and the purpose of determining the quality of the titration of long-acting insulin though, it is important to detect trends over a certain period of time as common treatment algorithms for long-acting insulin rely mainly on morning fasting values.

Therefore, the need exists to provide a reliable trend indicating method for a plurality of measurement values, providing a trend analysis over a midrange time interval, which is easy to understand for the patient and useful to the HCP when adjusting the prescribed therapy.

Document WO 2011/007051 A1 discloses a method for controlling the measurement process of blood glucose of a patient and a respective arrangement wherein a first average value of the blood glucose level difference of a measurement value pair, that means of values taken before a meal and after a meal, over a recent first block of three days is calculated and compared to a second average value of such a difference of a second block of three days prior the recent three days. From the comparison of the first and second average value a trend may be determined which is, however, very brittle to outliers.

Documents U.S. Pat. No. 7,904,310 B2 and U.S. Pat. No. 7,853,455 B2 disclose a system and method that enables a health care provider to monitor and manage a health condition of a patient wherein the user can select graphic display of blood glucose test results over a specific period of time such as a particular week. When such a weekly trend graph is displayed, small icons identify points on the graphic representation that correspond to the blood glucose test results, wherein coordinate values for blood glucose level and measurement time of day can be displayed if desired. Further, the graph consists of lines interconnecting points that correspond to the blood glucose test results and the average blood glucose level as well as the standard deviation of the measurement values may be displayed. For people without higher mathematical education the interpretation of such a graph, the average value and the standard deviation is too difficult.

Documents WO 2010/149392 A1 and EP 2 486 851 A1 disclose a method and system for providing an estimated true mean blood glucose value from spot blood glucose measurements. This system comprises a display, memory and a processor program to collect spot blood glucose measurement values and associated context of the blood glucose measurements at daily times and events specified by a structured sampling schema provided in memory, to weight each of the connected blood glucose measurement values based on the associated context and to determine the estimated true mean blood glucose value from the weighted measurements of the collected blood glucose measurements and to provide the estimated true mean blood glucose value to the display. Any trend information cannot be derived from these true mean blood glucose values.

Documents WO 03/057027 A2 and EP 2 259 057 A1 refer to a system for monitoring physiological characteristics according to the user biological state comprising a sensor input capable of receiving a signal from a sensor, the signal being based on a sensed physiological characteristic value of a user, a memory for storing a plurality of measurements of the sensed physiological characteristic value of the user from the received signal from the sensor and a display for presenting a graphical representation of the plurality of measurements of the sensed physiological characteristic value preferably continuously in real time. Further, the graphical representation may comprise one or more trend indicators indicating an approximate rate trend in the sensed physiological characteristic value over a recent series of the plurality of measurements. Therefore, different trend values are defined, for example a high positive trend threshold which defines a limit at 3 mg/dl per minute averaged over 20 minutes. A low positive trend threshold defines a limit at 1 mg/dl per minute, a high negative trend threshold a limit at −3 mg/dl per minute and a low negative trend threshold a limit at −1 mg/dl per minute, each averaged over 20 minutes. This prior art method of trend representation is only useful for continuous measurement of blood glucose level.

Document EP 2 031 534 A1 refers to a diabetes management system and process that may be used to analyze and recognize pattern for a large number of blood glucose concentration measurements and other physiological parameters related to the glycemia of a patient. It is disclosed that a display area includes a graphical pattern of blood glucose variability about a median blood glucose value by at least one of time of day, of day in a week, of both time of day and day of week, or at different predetermined intervals. A diagram shows a graphical blood glucose variability pattern in relation to a specific day as spanning from 24 hours starting at about 12 a.m. to about 12 a.m. of the next day. Therein, the median of glucose concentration values and a median of test times during this temporal period are shown defining a data point on a graph depicted by a bold line. As one can derive from the respective diagram such a trend representation is rather difficult to interpret by the patient.

Hence, the object of the present invention is to provide a data management unit and a respective method which avoids the above drawbacks and provides information for self-monitoring of a physiological parameter containing reliable trend information which is easy to understand by the patient and useful to the HCP when adjusting the prescribed therapy.

The above problem is solved by a data management unit with the features of claim 1.

In particular the inventive data management unit for supporting health control comprises
a data storage adapted to store a plurality of measurement values of a physiological parameter, for example the fasting blood glucose level, and for each measurement value an associated time stamp, and
a trend indicator, wherein the trend indicator is adapted to indicate different trend categories, for example an increasing trend, a steady trend and a decreasing trend, preferably as a respective visible sign on a display and/or as a respective audible signal by a loudspeaker,
a processor adapted to select a first group of measurement values and a second group of measurement values from the plurality of measurement values of the data storage such that the associated time stamp of each of the measurement values of the first group is in a predefined first time interval and the associated time stamp of each of the measurement values of the second group is in a predefined second time interval, wherein the second time interval is more recent than the first time interval, wherein the processor is further adapted to calculate a first mean value as a median from the first group of measurement values and a second mean value from the second group of measurement values,
wherein the processor interacts with the trend indicator such that the trend indicator indicates one of the different trend categories, for example the increasing trend, the steady trend or the decreasing trend, based at least in part on a result of a comparison of the second mean value to the first mean value.

The time stamp associated to each measurement value comprises date and time information of a certain time point during the measurement process resulting in the respective measurement value, for example the completion of the measurement process. The first and the second time interval mentioned above refer to an interval including both, the date and time information of the time stamp. If, for example the second time interval is defined as the recent 3 days the second group contains all measurement values with the time stamp referring to the present day and the two days before (days 0, −1 and −2). Accordingly, if, for example the first time interval is defined as the 7 days before the recent 3 days the first group contains all measurement values with the time stamp referring to the days −3 to −9.

In an embodiment the trend is calculated and indicated with regard to the fasting blood glucose level considering fasting blood glucose measurement values of the first and second time interval only. Indicating the trend with regard to this physiological parameter is particularly interesting and helpful as this parameter is an outstanding parameter and often used for titration of basal long-acting insulin as explained above.

The comparison of the second mean value to the first mean value is preferably executed by calculation of a difference of both values.

The inventive data management unit on the one hand provides the patient with trend information that is robust to exclude outliers from any potential consideration to adjust therapy because the median of the first group of measurement values is used as basis for comparison. The median is the middle measurement value of the first group when the measurement values are ranked in order. If there is an even number of measurement values in the first group, the arithmetic mean of the middle two measurement values is taken. Alternatively, one value of the middle two measurement values is taken. For example, either the lower value is taken or the higher value is taken, or the most recent value is taken.

Further, the inventive unit is in particular useful for self-monitoring spot measurements wherein a comparatively small number of measurement values per middle-size time interval comprising some days is received. Additionally, because only one of different trend categories, for example the increasing trend, the steady trend or the decreasing trend, is displayed dependent on the comparison of the second mean value to the first mean value, it is easy to understand for the patient even without higher mathematical education. Additionally, the inventive data management unit providing trend information gives the patient information to continue to adhere with therapy and/or to continue behavior that leads to desired trends.

Accordingly, the above problem is solved by a medical device for supporting health control, the device comprising the above explained data management unit.

The above problem is also solved by a system comprising the above mentioned medical device and a case adapted to carry and secure the medical device and preferably a box containing test strips and/or a lancet. The case further comprises additionally at least one flash card containing information related to the use of the device, preferably with regard to the different trend categories or tags as well as to the operation of the medical device. In an embodiment the at least one flash card is fixed by two rings or a hinge to the case so that an easy access is provided for the user/patient to the information contained at the backside of such a flash card by hinging down the respective card. In this position the card is still fixed to the case and therefore cannot get lost.

For the same reason the above problem is also solved by a method for indicating a trend within a plurality of measurement values of a physiological parameter stored in a data storage, wherein each measurement value is stored with an associated time stamp, comprising
- selecting a first group of measurement values and a second group of measurement values from the plurality of measurement values such that the associated time stamp of each of the measurement values of the first group is in a predefined first time interval and the associated time stamp of each of the measurement values of the second group is in a predefined second time interval, wherein the second time interval is more recent than the first time interval,
- calculating a first mean value as a median from the first group of measurement values,
- calculating a second mean value from the second group of measurement values, and
- indicating one of different trend categories, preferably as a respective visible sign on a display and/or as a respective audible signal by a loudspeaker, based at least in part on a result of a comparison of the second mean value to the first mean value, preferably based on a difference of the first mean value and the second mean value.

In another embodiment of the data management unit or trend indicating method the first time interval is larger than the second time interval, preferably the first time interval has seven days and the second time interval has three days. The larger first time interval provides a better statistical approach for the comparison with the recent measurements. Further, the patient still remembers what happens on recent three days and a seven day period is meaningful for potential therapy adjustments.

In another embodiment of the data management unit or trend indicating method the second mean value is the arithmetic mean value of the measurement values of the second group which is an easily computable mean value for a smaller number of measurement values. Alternatively, a geometric mean value or a harmonic mean value may be used.

In another embodiment of the data management unit or trend indicating method the data storage further stores a relative tolerance range of the second mean value, preferably 15% or 20% or 25% of the second mean value, wherein the trend indicator is adapted to indicate one predefined of the different trend categories, for example the steady trend, if the result of the comparison is within the relative tolerance range, preferably if the second mean value is greater than a predefined low limit. The advantage of providing a tolerance range is that otherwise the indicated trend would be confusing, for example by changing too frequently. The aim of the data management is to be on the safe side for the patient. Further, the definition of the relative tolerance range is more useful if the most recent second mean value is above a predefined low limit. In case the second mean value is below the low limit the relative tolerance range value would be too small.

In an example embodiment of the data management unit or trend indicating method the data storage further stores an absolute tolerance range, wherein the trend indicator is adapted to indicate one predefined of the different trend categories, for example the steady trend, if the result of the comparison is within the absolute tolerance range, preferably if the second mean value is less than or equal the predefined low limit. Preferably, if the second mean value is so small that it is below or equal to the predefined low limit it is useful to define an absolute tolerance range in order to prevent confusing up and down change of the trend indication.

For a fasting blood glucose trend calculation the predefined low limit may be chosen between 100 mg/dl and 150 mg/dl, preferably at 125 mg/dl.

In another embodiment of the data management unit or trend indicating method the second time interval includes the present day so that the trend calculation is as up-to-date as possible.

In another embodiment of the data management unit or trend indicating method the first time interval and the second time interval do not overlap so that the first mean value and the second mean value are calculated based on fully different measurement values. Otherwise the one or more measurement values of the overlapping time interval would be weighted more than the other measurement values.

In another embodiment of the data management unit or trend indicating method the processor interacts with the trend indicator such that in case less than a predefined first number limit of measurement values is in the first time interval and/or less than a predefined second number limit of measurement values is in the second time interval the trend indicator does not indicate the one of the different trend categories, for example the increasing trend, the steady trend and the decreasing trend, in this case preferably the trend indicator is adapted to indicate an error as there are not enough measurement values to provide a good statistics. With regard to the fasting blood glucose level as the physiological parameter the first number limit is 5 or more, preferably 7 or 9, and the second number limit is 2, 3 or 5, also dependent on the definition of the first number limit.

In another embodiment of the data management unit or trend indicating method the trend indicator is adapted to show on the display an up arrow as the increasing trend sign, a down arrow as the decreasing trend sign and a horizontal arrow as the steady trend sign. These signs are easy to understand for the user/patient.

In another embodiment of the data management unit or trend indicating method the data storage is further adapted to store an associated event tag for each measurement value in order to further categorize the measurement values, and the event tag is considered additionally for selection of the first group of measurement values and the second group of measurement values from the plurality of measurement values. For example blood glucose measurement values could be categorized as fasting blood glucose measurement value, as a pre-meal blood glucose measurement value or a past-meal blood glucose measurement value, or as a measurement value of a control solution or with a no-tag. By using such an event tag it can be guaranteed that only (the mean values of) the measurement values of the same category, e.g. the fasting blood glucose measurement values, are compared.

For the same reason as explained above the above problem is solved by a computer program for indicating a trend within a plurality of measurement values of a physiological parameter stored in a storage, wherein each measurement value is stored with an associated time stamp, the computer program comprising:
  code for selecting a first group of measurement values and a second group of measurement values from the plurality of measurement values such that the associated time stamp of each of the measurement values of the first group is in a predefined first time interval and the associated time stamp of each of the measurement values of the second group is in a predefined second time interval, wherein the second time interval is more recent than the first time interval,
  code for calculating a first mean value as a median from the first group of measurement values,
  code for calculating a second mean value from the second group of measurement values, and
  code for indicating one of the different trend categories, for example an increasing trend, a steady trend or a decreasing trend, preferably as a respective visible sign on a display and/or as a respective audible signal by a loudspeaker, based at least in part on a result of a comparison of the second mean value to the first mean value.

The above computer program may be realized with the embodiments as mentioned above with regard to the inventive trend indicating method.

The above problem is further solved by a computer program product comprising a computer-readable medium bearing computer program code embodied therein for use with a computer, wherein the computer program code comprises the above mentioned computer program.

Figure 2:
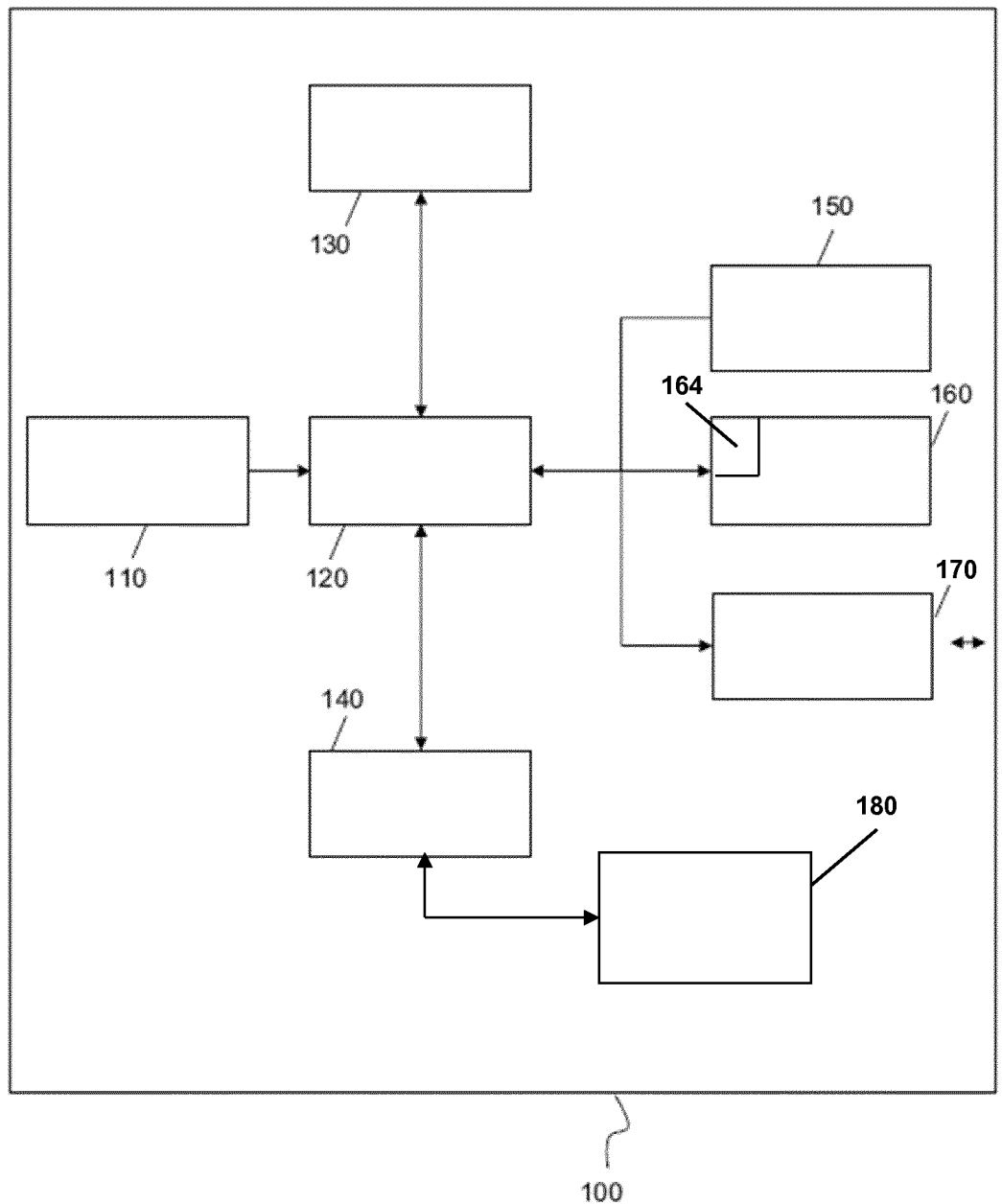
Figure 3:
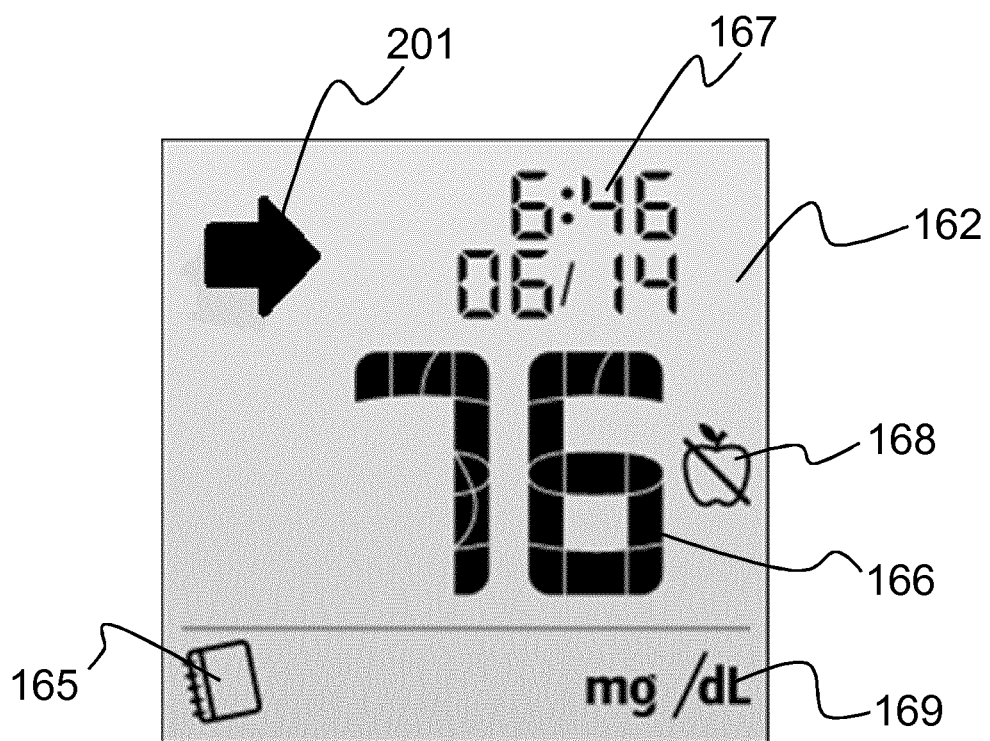
Figure 4:
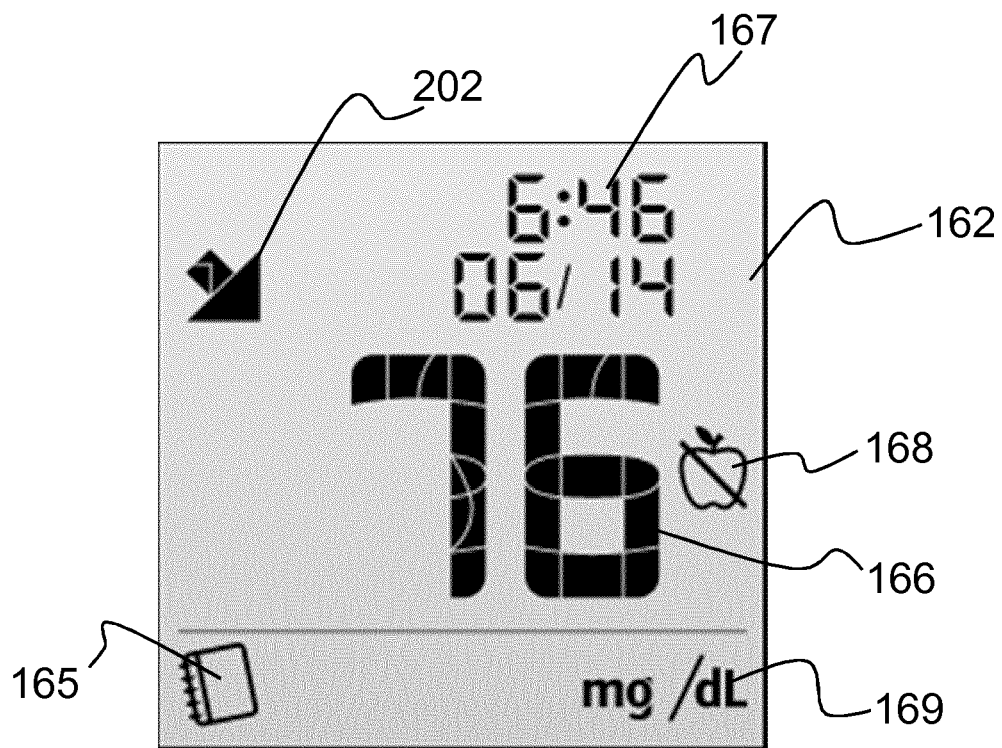
Figure 5:
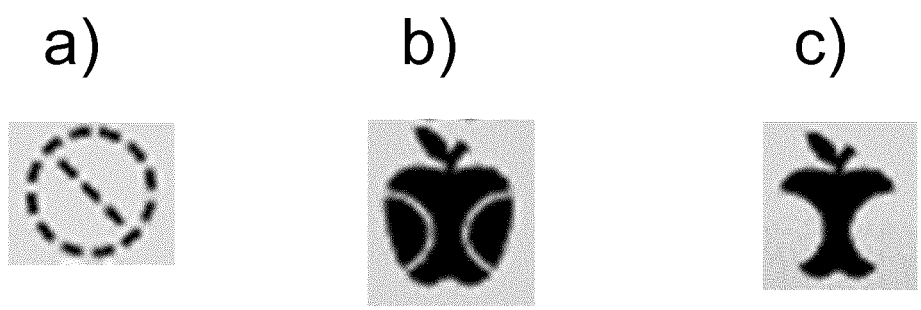
Figure 6:
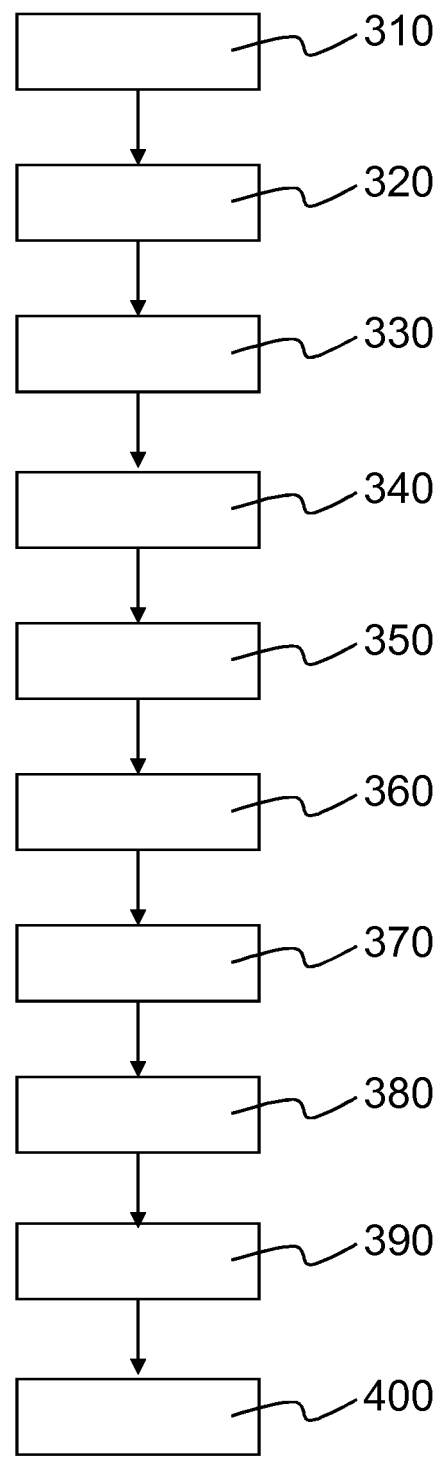
Figure 7:
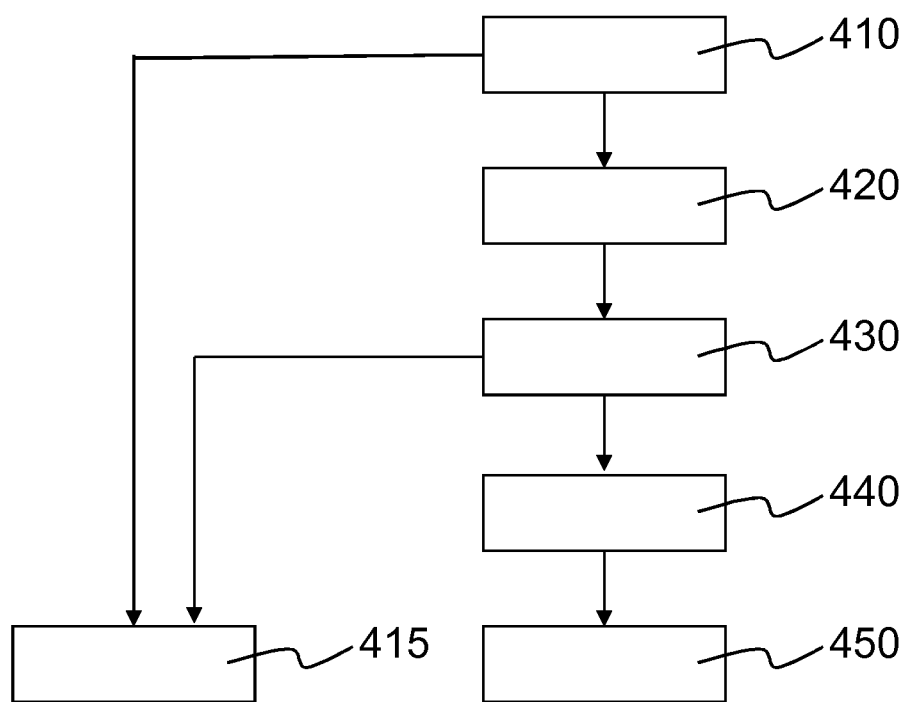
Figure 8:

The above-mentioned advantages as well as other advantages of various aspects of the present invention will become apparent to those of ordinary skill in the art by reading the following detailed description with the explanation of the accompanying drawings. All features described above and below and/or illustrated per se or in any combination form the subject-matter of the invention, independent of their inclusion in the claims or their back-reference. Exemplary embodiments of the present invention are described herein with reference to schematic drawings, in which FIG. 1 shows the medical device according to a preferred embodiment of the invention in a perspective view;

FIG. 2 shows a diagram of the medical device as shown in FIG. 1;

FIG. 3 a first example of the display of the medical device as shown in FIG. 1 in a "Logbook" mode;

FIG. 4 a second example of the display of the medical device as shown in FIG. 1 in a "Logbook" mode;

FIG. 5 further examples of tag signs as they are displayed on a display of the medical device as shown in FIG. 1;

FIG. 6 a flow diagram containing a procedure realized by the inventive medical device in the "Measure BG" mode;

FIG. 7 another flow diagram comprising an embodiment of the inventive method for indicating a trend; and FIG. 8 an inventive system comprising a case and the medical device according to FIG. 1 in a top view, wherein the case is in an open state.

The following paragraphs will describe various embodiments of the invention. For exemplary purpose only, the embodiments are outlined in relation to a medical device supporting health control and the trend indication method with regard to blood glucose level measurement, in particular with regard to fasting blood glucose level measurement. However, the used terminology and the description of the embodiments with respect to the medical device or health indicating method are not intended to limit the principles and ideas of the invention to such a single device or method and may be adapted to other physiological values accordingly.

FIG. 1 is a schematic drawing and FIG. 2 is a schematic diagram of the medical device 100 according to a preferred embodiment of the invention. Preferably, the medical device 100 comprises a blood glucose measurement unit 110, which is arranged to measure the blood glucose level. Further, the measurement unit 110 comprises an interface and a slot 112 for inserting a test strip.

The blood glucose measurement unit 110 is connected to a receiving unit 120, which is arranged to forward e.g. blood glucose measurement data received from blood glucose measurement unit 110 to a data storage 130 (storage unit or means) or memory, such as a Flash memory. Alternatively, the receiving unit 120 may retrieve stored data such as e.g. blood glucose value data from the storage 130 and forward it to a processor 140 (processing unit or means), such as a microcontroller or microprocessor, a digital signal processor, and/or the like. Alternatively, the receiving unit 120 directly forwards the blood glucose value data received from the blood glucose measurement unit 110 to the processor 140.

Receiving unit 120 is further connected to a user input unit 150 of a user interface. The user input unit 150 is arranged to receive input from the user of the medical device 100 for example by key 151, confirmation key (OK button) 152, key 153 for scrolling down (downward button) and key 154 for scrolling up (upward button). The user input data are forwarded from the user input unit 150 to the receiving unit 120, which either forwards it to the processor 140 or to the data storage 130.

Furthermore, the user interface of medical device 100 comprises a display unit 160 with a display 162, which is connected to the receiving unit 120 as well. Preferably, the display unit 160 receives data to be displayed by the display 162 from the receiving unit 120 or the processor 140.

Preferably, the medical device 100 additionally comprises a further interface 170, for example a wired interface such as a serial port, a Universal Serial Bus (USB) interface, a mini-USB interface, or a wireless interface such as an infrared (e.g. an IRDA) interface, a Bluetooth™ interface, and/or the like, in order to receive data and/or to transmit data. The interface 170 is preferably connected to the receiving unit 120 in order to receive data from the receiving unit 120 and/or to forward data to the receiving unit 120.

Additionally, the medical device 100 comprises a clock unit 180 which provides a date and time information, preferably based on a clock generator, which may be displayed at the display 162. Further, the clock unit 180 provides date and time information in particular for generating a time stamp for an associated blood glucose measurement.

As outlined above, the medical device 100 preferably comprises a blood glucose measurement unit 110. Preferably, the blood glucose measurement unit 110 is arranged to measure the blood glucose level in the blood of e.g. the user by testing a drop of blood on a test strip that is inserted into the slot 112. The measurement may be made by e.g. an electrochemical method or an optical method. Full insertion of the test strip in the slot 112 may be detected by a respective sensor. The measured blood glucose value is transformed to blood glucose value data and forwarded preferably immediately or on demand to the receiving unit 120. Alternatively, the blood glucose measurement unit 110 is arranged to measure the blood glucose level of the user via infrared diagnosis or an alternative contactless measurement method.

According to a further alternative (not depicted in FIG. 1) the blood glucose measurement unit 110 is implanted in the body of the user of the medical device and forwards the data to the receiving unit 120 either via a wired connection or via a wireless connection. In an embodiment, such an implanted blood glucose measurement unit 110 is a continuous measurement sensor e.g. based on a chip which may allow a continuous closed loop control. In the latter case the medical device comprises two parts, one part contains the measurement unit 110 and the other part the remaining units of the medical device. The blood glucose measurement unit 110 preferably forwards the blood glucose measurement value data to the receiving unit 120 via interface 170. According to a further alternative the medical device does not comprise a blood glucose measurement unit which measures the blood glucose values, but receives blood glucose value data from an external unit.

The measurement of the blood glucose measurement is preferably triggered by the receiving unit 120 which sends a respective signal to the blood glucose measurement unit 110. According to one preferred alternative the receiving unit 120 receives a trigger signal generated by user input which is received via user input unit 150 or based on a signal from the slot 112 detecting a test strip. Alternatively, the trigger signal is generated automatically by the clock unit 180 or by the processor 140.

Preferably, the receiving unit 120 is represented e.g. by the input ports and output ports of a microprocessor or a bus system managing the data handling between several functional units. This includes bus systems, such as e.g. Advanced Microprocessor Bus Architecture bus systems implemented in a microprocessor or external bus systems connected to a microprocessor. Via the receiving unit 120, data are retrieved from the data storage 130 on demand and forwarded to the processor 140, to the display unit 160 or to the interface 170. Moreover, the receiving unit 120 forwards control signals, such as trigger signals or control signals e.g. to the blood glucose measurement unit 110, the display unit 160 or the interface 170.

The data storage 130 is arranged to store data entered via the user input unit 150, a plurality of blood glucose measurement data received from the blood glucose measurement unit 110 together with the time stamp and/or at least one event tag associated to each measurement data, data calculated from the plurality of blood glucose measurement values processed by the processor 140 and/or data received via interface 170.

Further the data storage 130 stores parameter data like an associated time range for tagging preselection regarding for example a fasting tag, a pre-meal tag or a post meal tag. Preferably such a time range is defined using a center time and a duration, wherein the time range comprises the time around the center time with the size of ½ duration in both directions. For example, the time range for fasting tagging preselection is defined with a duration of 2 hours and a center time at 7 a.m., so that the time range for fasting tagging preselection encompasses the time between 6 a.m. and 8 a.m.

Additionally, for example the data storage 130 stores the following preset time ranges for pre- and post-meal times, preferably for tagging preselection:
pre-meal breakfast: 5:00 a.m. to 8:59 a.m.
post-meal breakfast: 9:00 a.m. to 10:59 a.m.
pre-meal lunch: 11:00 a.m. to 11:59 a.m.
post-meal lunch: 12:00 p.m. to 3:59 p.m.
pre-meal supper: 4:00 p.m. to 6:59 p.m.
post-meal supper: 7:00 p.m. to 8:59 p.m.
night time or bedtime: 9:00 p.m. to 11:59 p.m.

Mealtime and fasting time ranges may be settable by the user "Settings" mode of the medical device.

Furthermore, data storage 130 is arranged to provide the stored data to the processor 140, to the display unit 160 and/or to the interface 170. The data storage 130 is preferably implemented as a semiconductor memory such as a Flash memory. Alternatively, it is implemented as a hard disk memory or an on-chip memory of the processor 140.

The processor 140 is preferably a microprocessor or any other functional unit capable of processing data.

The user input unit 150 is preferably implemented as a keyboard comprising one or more push buttons 151, 152, 153, 154. The keyboard may comprise one or more soft keys, wherein the function of the soft keys may be displayed on the display 162. Alternatively, the user input unit 150 is a key board or a touch screen. Alternatively, the user input unit 150 comprises a microphone for receiving speech input so that data can be entered via speech input.

After a blood glucose measurement a tag may be associated to the measurement value referring to lifestyle data by pressing the up or down keys 153, 154 scrolling upwards or downwards through the different tags which are for example the fasting tag, pre-meal tag, post-meal tag and no-tag respectively referring to a measurement value which is a fasting blood glucose value, a pre-meal blood glucose value, a post-meal blood glucose value and a blood glucose value that cannot be associated to one of the previous lifestyle parameter.

The display unit 160 preferably comprises an LCD or LED display 162. Preferably, the display displays a number of alphanumerical characters so that e.g. the presently measured blood glucose value can be displayed together with additional instructions for the user. Alternatively or additionally, the display unit 160 comprises a graphic display in order to display graphs or graphics such as icons. Further the display of the display unit 160 may comprise a touchscreen.

The display unit 160 further may also show a trend indicator 164 (trend indicating unit or means) which is adapted to indicate different trend categories, for example an increasing trend, a steady trend and a decreasing trend, symbolized e.g. as an arrow pointing up, an horizontal arrow 201 and an arrow pointing down 202, respectively, at the display 162 (see FIGS. 3 and 4). Alternatively or additionally, the trend may be communicated by a loud speaker, wherein the increasing trend may be represented by a tone with an increasing pitch, the steady trend by a tone with a constant pitch and the decreasing trend by a tone with a decreasing pitch.

The interface 170 is preferably a wireless interface, such as IRDA, Bluetooth™, GSM, UMTS, ZigBee, or WI-FI, etc. Alternatively, the interface is a wired interface, such as a USB port, mini-USB port, serial data port, parallel data port, etc., for receiving and transmitting data. In a further alternative embodiment the medical device 100 does not comprise an interface 170.

According to another alternative embodiment, medical device 100 comprises a memory card reader or a memory card reader interface. The memory card reader is preferably adapted to read information from a memory card, such as a Flash memory card, or any type of SIM card. For this purpose, the memory card comprises a memory, wherein at least one of selected algorithms together with corresponding parameters, a history of the blood glucose values and/or insulin doses administered, etc. is stored. Thus, in the case that the medical device 100 has a defect, the relevant data may still be stored on the memory card which can be easily removed from the memory card reader of the medical device 100 and transferred to a new medical device 100. Moreover, the memory card 100 may be used in order to provide information on the history of the treatment to e.g. an HCP.

In the case that the memory card is a SIM card providing subscriber identification for a mobile communication network and the interface unit 170 is additionally a mobile communication interface, additional functions of the medical device 100 can be unlocked by the provider of the SIM card via a telecommunication channel. This offers the possibility that the medical device 100 can communicate with other telecommunication devices via predefined channels, such as UMTS or GSM. Via the international mobile subscriber identity, also called IMSI, stored in the SIM card, the medical device 100 identifies itself within the network and, thus, can be addressed via the network. In such a case the medical device 100 can be easily checked, remote controlled, updated, monitored, etc., via interface unit 170, e.g. by addressing the mobile communication unit with a phone number.

Furthermore, the medical device 100 is able to transmit data via SMS, e-mail or via mobile internet connection. Moreover, this offers the possibility to locate the medical device 100 in an emergency case.

In the case that the blood glucose measurement unit 110 is a continuous sensor which is e.g. implanted a dose delivery unit with an insulin pump forming an automatic delivery system may be additionally provided.

As shown in FIG. 6, the medical device 100 is capable to perform a number of operating processes. According to a preferred alternative after switching on, e.g. by pressing a key 151, 152, 153 or 154, preferably the confirmation key 152 for a predetermined time, or detection of a test strip within the slot 112, the medical device 100 performs initialization step 310 for initializing the functional components of the medical device 100. After this, the different operation modes which are implemented in the medical device 100, are displayed in the display step 320, preferably operation modes such as "Measure BG", "Logbook" and/or "Settings".

In step 330 the user selects one of the displayed operation modes via the user input unit 150, for example by means of the keys 153, 154 for scrolling down or up, and confirms the selection using the confirmation key 152.

In step 340 the selected operation mode is executed. As an example the mode "Measure BG" is selected for executing a blood glucose measurement. Upon execution of this mode the user/patient is requested to provide a test strip with a blood sample.

In the "Logbook" mode the history of previous measurements and statistical results may be calculated and displayed. The "Settings" mode allows the user to define and change some parameters of the medical device 100.

After selecting the mode "Measure BG", in step 350 a drop of blood is applied to the test portion of the test strip which is inserted in slot 112 of the medical device 100.

According to an alternative version of the operation process steps 310 to 340 may be skipped in the case that a specific operation mode is preselected. In this case, after initialization, the preselected operation mode, which is either preselected by the user or automatically selected in accordance with a specific event, for example the detection of a fully inserted test strip in slot 112, the operating process proceeds with the following step 350 and asks the user to apply a drop of blood. In step 360 it executes the preselected one or more operation modes, for example the mode "Measure BG".

Now in step 360 the measurement unit 110 determines e. g. by an electrochemical method the blood glucose level and displays the respective measurement value at the display 162. In the next step 370 the clock unit 180 generates the time stamp of the present measurement comprising a date and time information. The time stamp is also displayed in display 162 and both, the present blood glucose measurement value and the associated time stamp is transferred by receiving unit 120 to the data storage 130.

In the next step 380 the processor 140 compares the time stamp of the present blood glucose measurement value with the time ranges of the events stored in the data storage 130 which events may be selected as the associated event tag. If the time stamp of the present measurement value, in particular the time information of the time stamp, lies within the current time range of e. g. the fasting event automatically the fasting tag is provided for confirmation by the user and displayed with a respective sign 168, for example a struck out, empty apple, at display 162. In order to show that a confirmation is necessary the tag sign 168 displayed on display 162 is blinking/flashing. Now, the user may confirm the fasting tag for example by pressing the confirmation key 152. Alternatively, the user may change the tag using the up and down keys 153, 154 into the pre-meal tag, the post-meal tag or the no-tag (nil). If the correct tag is chosen the user confirms the tag by pressing the confirmation key 152. By confirmation of the tag with the confirmation key 152 the flashing of the displayed tag sign is stopped and the tag sign is displayed continuously without blinking. In this state, pressing the up/down keys 153, 154 will not change the tag. Then, the processor 140 initiates storage of the associated, confirmed tag with regard to the recent measurement value in the data storage 130 via receiving unit 120.

If in step 380 the processor 140 cannot find any range for tagging pre-selection which refers to the time information of the time stamp of the present measurement value, the no-tag is preselected.

After pressing the confirmation key 152, if the user presses the confirmation key again, the tag will start flashing again and pressing the up/down key will again allow the user to change the tag as explained above.

Further, in the "Logbook" mode the user is allowed to change the tag in the above explained manner but only within a predefined time range from the associated time stamp of the blood glucose measurement value, for example within 10 days.

If the time stamp of the recent measurement value falls within the current time range for tagging pre-selection and there is already a measurement value in that day marked as fasting the fasting tag is not automatically displayed and not selectable and therefore may not be associated to the recent measurement value.

Further, if, for example the fasting time range for tagging preselection overlaps with, for example the time range for pre-meal breakfast, the fasting tag has priority over the pre-meal tag. Hence, in this case, if no fasting value is recorded for that day, the fasting tag is automatically pre-selected if the time stamp of the present measurement value lies within the time range for the fasting tag and the time range for pre-meal breakfast.

In another embodiment a flashing tag may not only be confirmed by the user by pressing the confirmation key 152 but also by removal of the strip from the port 112 after a blood glucose test, or when the medical device goes into sleep mode.

In the next optional step 390 a comment to the present measurement value may be selected by the user using the up and down keys 153, 154. The comment may then be confirmed with the confirmation key 152, wherein the chosen comment is then stored in the data storage 130 associated to the present measurement value as well.

In step 400 after each measurement (and finishing tagging in step 380) the processor 140 compares whether the time information of the time stamp of the last e.g. three consecutive measurement values tagged with the same event tag, for example with the fasting tag, including, if applicable, the present measurement value are outside the current time range for tagging pre-selection of the fasting event in the same direction. If not all three associated time stamps are outside the current time range in the same direction the current time range for tagging preselection of the fasting tag stored in the data storage 130 is not changed. If the processor 140 detects that all three time stamps of the three consecutive previous measurement values tagged with the fasting tag are outside the current time range in the same direction (i.e. all three time stamps exceeds the time range above or below) the time range is shifted. Therefore, the arithmetic mean value of the time information of the three time stamps is calculated and used as the new center time for the time range for tagging pre-selection of the fasting tag. The duration of the time range may stay the same.

For example, the time information of the time stamps of the recent 3 measurement values comprising the fasting tag are 8:10 a.m., 8:27 a.m. and 8:23 a.m. and the present time range for fasting tag preselection refers to a center time at 7 a.m. and a duration of 2 hours. Then, in step 400 the processor 140 determines that all time information is outside the current time range for fasting tag preselection in the same direction. In this case the time range for fasting tagging preselection is changed to a center time at 8:20 a.m. which is the arithmetic mean value of the three time stamps. This new current time range center value is then stored in the data storage 130. Hence, the time range now is between 7:20 a.m. and 9:20 a.m., as the duration is not changed, so that if the user now measures a blood glucose value within this time range automatically the fasting tag sign is displayed after finishing measurement for user confirmation.

The above explained method to adjust the time range for fasting tag preselection provides a comfortable way to cope with the user's/patient's needs and to ease the tagging procedure. Hence, correct tagging is supported by the above procedure.

The above explained adjustment may be analogously used with other tags and respective time ranges as well.

When the medical device 100 is in the "Measure BG" mode, the device may turn into the sleep state automatically after for example 120 seconds without any new action. Once the device has returned a new measurement value, the device turns to the sleep state automatically after for example 60 seconds without any user interaction.

As explained above the medical device 100 provides at least one memory review mode which is called "Logbook" mode. The respective display and calculations are explained in the following.

The "Logbook" mode is entered when the user activates the medical device 100 by pressing e.g. the confirmation button 152. Then a display as depicted in FIGS. 3 and 4 is shown.

In the "Logbook" the measurement values preferably are preferably displayed in the order in which the entries are entered into the device, or alternatively according to the time and date assigned to the measurement values. In particular the most recent blood glucose measurement value is shown upon entry into the "Logbook" mode. Pressing the up and down keys 153, 154 the user may scroll through the records, for example by pressing the down key 153 the user may scroll backwards in time and by pressing the up key 154 the user scrolls forward in time.

Examples of a display 162 showing a measurement value are shown in FIGS. 3 and 4. The user knows from the "Book" sign 165 in the lower left corner of the display that he/she has entered the "Logbook" mode.

The display 162 in the "Logbook" mode further shows the blood glucose measurement value 166 as biggest number in the center of the screen. Above the measurement value 166 the associated time stamp 167 including date and time is displayed. On the right side the associated tag as a sign 168 is provided, wherein the sign may show for example an empty, struck out apple as shown in FIGS. 3 and 4 in case of an associated fasting tag, a full apple as shown in FIG. 5*b*) in case of an associated pre-meal tag, a bitten apple as shown in FIG. 5*c*) in case of an associated post-meal tag or a struck out circle as shown in FIG. 5*a*) in case of an associated no-tag. Additionally, in the lower right corner of the display 162 the measurement unit 169 for the blood glucose value is provided.

The upper left corner of the display 162 in the "Logbook" mode shows a sign representing a trend for fasting blood glucose values controlled by the trend indicator 164 which is activated in the "Logbook" mode. The trend indicator 164 shows the trend of the respective fasting blood glucose measurement value using an arrow pointing up, an arrow pointing horizontally 201 (see FIG. 3) or an arrow pointing down 202 (see FIG. 4).

The operating process of the medical device 100 for trend indication is explained in the following and is depicted in FIG. 7.

For each fasting measurement value the processor 140 selects in step 410 via the receiving unit 120 from the data storage 130 a second group of measurement values containing the fasting tag of the recent e.g. three days, for example the fasting measurement values of the present day and the two days before (days 0, −1 and −2), wherein at least two fasting measurement values within the three day period must be available. If less than two fasting measurement values, i.e. only one fasting measurement value, within the three day period is available the procedure moves to step 415 and the trend indicator 164 does not calculate and display a respective trend arrow and the display 162 stays empty in the upper left corner or shows an error sign.

Then, in step 420 the arithmetic mean value is determined from these 3 or 2 fasting measurement values as the second mean value CURR_FAST_AVG.

Further in step 430, the processor 140 selects from the data storage 130 via the receiving unit 120 a first group of measurement values based on the associated time stamp comprising seven days before the recent three days, i.e. three days to nine days prior the recent fasting measurement value (days −3 to −9), wherein at least a first number limit of for example 5 fasting measurement values within the seven day period must be available. Otherwise, the procedure moves to step 415 and the processor 140 does not calculate a trend and the trend indicator 164 does not display any trend arrow or shows an error sign.

In step 440, if there are enough fasting measurement values, from the fasting measurement values of the first group the median is determined as a first mean value PAST_FAST_MED.

Now, in the next step 450 the trend is calculated and displayed using respective arrows in the following way.

If the second mean value CURR_FAST_AVG is greater than a low limit of 125 mg/dl and the difference between the second mean value and the first mean value is greater than 20% of the second mean value (corresponding to a relative tolerance range), i.e.

(CURR_FAST_AVG−PAST_FAST_MED)>(CURR_FAST_AVG*20%), the fasting trend up arrow is displayed on the display 162.

Also, the fasting trend up arrow is displayed on the display 162 if the second mean value CURR_FAST_AVG is less than or equal the low limit of 125 mg/dl and the difference between the second mean value and the first mean value is greater than 25 mg/dl (corresponding to an absolute tolerance range), i.e.

(CURR_FAST_AVG−PAST_FAST_MED)>25 mg/dl.

If the second mean value CURR_FAST_AVG is greater than the low limit 125 mg/dl and the difference between the first mean value and the second mean value is greater than 20% of the second mean value (corresponding to the relative tolerance range), i.e.

(PAST_FAST_MED−CURR_FAST_AVG)>(CURR_FAST_AVG*20%), the fasting trend down arrow 202 is displayed on the display 162.

Also, the fasting trend down arrow 202 is displayed on the display 162 if the second mean value CURR_FAST_AVG is less than or equal the low limit of 125 mg/dl and the difference between the first mean value and the second mean value is greater than 25 mg/dl (corresponding to an absolute tolerance range), i.e.

(PAST_FAST_MED−CURR_FAST_AVG)>25 mg/dl.

If there is a valid calculation, i.e. at least two fasting measurement values in the second group and at least 5 fasting measurement values in the first group of measurement values, in all other cases the fasting trend steady arrow 201 is displayed by the trend indicator 164 at the display 162.

The fasting trend arrows showing in upward, downward or horizontal direction are easy to understand for the patient and provide a reliable and descriptive assessment of the fasting blood glucose value development over a time range of about 1.5 weeks.

In an example embodiment, device 100 may be realized as a two-part device, wherein the data storage 130, the receiving unit 120, the processor 140, the user input unit 150, the display unit 160 with the trend indicator 164, the interface unit 170, and the clock unit 180 are realized as a software program (application or "app") to run on the hardware of a smartphone. The keys 151, 152, 153 and 154 are realized in this case as button fields on the display of a touchscreen.

FIG. 8 shows a case 500 for a medical device in an open state comprising the medical device 100, a box 502 with test strips and a lancet 504. In the example embodiment of FIG. 8, the case 500 is made of a textile material. In an alternative embodiment, the case may be made of a plastic material, a leather material, a combination of any of these materials, and/or the like. The medical device 100, the box 502 and the lancet 504 are fixed to left side the case 500 by means of flexible straps 505 so that each of these elements may be easily removed from the case 500.

On the left side of the case several flash cards 506 are fixed hingedly by two rings 508 to the case 500. Each ring 508 may be opened so that one card or more cards 506 may be removed from the case 500. Each flash card 506 provides important information to the user/patient like explanations and pictures with regard to the buttons, the display, the symbols of the display and their meaning, or the operation of the medical device 100, for example how to tag a measurement value. The flash card 506 provides such information on the front side, but may also provide information on the back side. In order to access the information printed on the backside of each card 506 it may be hinged down (pivoted around the axis of ring 508) by the patient/user so that the backside information is visible. Therefore, the information on the backside is inversely printed so that it is easily readable when the card is hinged down as it is shown in FIG. 8. For easy orientation each flash card 506 may be marked at a top area with a different color. The ring 508 further has the advantage that the card is still fixed to the case when the patient/user reads the backside so that the card cannot get lost. In the state where all flash cards 506 are pivoted such that they are positioned fully within the case 500 the case may be closed using the zipper 510. In the closed state of the case 500 the interior is well protected against environmental impact.

The invention claimed is:

1. A data management unit for supporting health control comprising:
   a measurement unit configured to generate measurement values of a physiological parameter in response to a trigger signal from a slot detecting a biological sample of a user;
   a clock generator communicatively coupled to the measurement unit and configured to automatically generate, for each of the measurement values of the physiological parameter, an associated time stamp;

a data storage communicatively coupled to the measurement unit and the clock generator and configured to store the plurality of measurement values of the physiological parameter, the plurality of measurement values comprising a fasting blood glucose level, the data storage also configured to store the associated time stamp for each measurement value;

a display unit that presents a visual element that corresponds to one of a plurality of different trend categories, the different trend categories comprising at least an increasing trend, a steady trend, and a decreasing trend; and one or more processors configured to:
   select a first group of measurement values and a second group of measurement values from the plurality of measurement values of the data storage such that the associated time stamp of each of the measurement values of the first group is in a predefined first time interval and the associated time stamp of each of the measurement values of the second group is in a predefined second time interval, wherein the second time interval is more recent than the first time interval;
   determine that a first count of measurement values in the first group satisfies a first threshold number and that a second count of measurement values in the second group satisfies a second threshold number, and in response:
      calculate a median value from the first group of measurement values;
      calculate a mean value from the second group of measurement values;
      calculate a difference between the mean value and the median value;
      determine one of the different trend categories based on the calculated difference;
      cause information about the determined trend category to be transmitted to a user, including causing the display unit to display the visual element that corresponds to the determined trend category; and
      provide guidance for the user to adjust the user's treatment based on the determined one of the different trend categories.

2. The data management unit according to claim 1, wherein the first time interval is larger than the second time interval.

3. The data management unit according to claim 2, wherein the first time interval encompasses seven days and the second time interval encompasses three days.

4. The data management unit according to claim 1, wherein the mean value is an arithmetic mean value of the measurement values of the second group.

5. The data management unit according to claim 1, wherein the data storage is configured to store a relative tolerance range of the mean value, the relative tolerance range being 15%, 20%, or 25% of the mean value, wherein the display unit presents the visual element that corresponds to one of the plurality of different trend categories if the result of the comparison is within the relative tolerance range.

6. The data management unit according to claim 5, wherein the one of the plurality of different trend categories is the steady trend, and the display unit presents the visual element that corresponds to the one of the plurality of different trend categories if the mean value is greater than a predefined low limit.

7. The data management unit according to claim 1, wherein the data storage is configured to store an absolute tolerance range, and the display unit presents the visual element that corresponds to the steady trend if the result of the comparison is within the absolute tolerance range.

8. The data management unit according to claim 7, wherein the display unit presents the visual element that corresponds to the steady trend if the mean value is less than or equal to a predefined low limit.

9. The data management unit according to claim 1, wherein the second time interval encompasses the present day.

10. The data management unit according to claim 1, wherein the first time interval and the second time interval do not overlap.

11. The data management unit according to claim 1, wherein the display unit is configured to present an up arrow as the visible element for the increasing trend category, a down arrow as the visible element for the decreasing trend category, and a horizontal arrow as the visible element for the steady trend category.

12. The data management unit according to claim 1, wherein the data storage is configured to store an associated event tag for each measurement value, and the event tag is considered for selection of the first group of measurement values and the second group of measurement values from the plurality of measurement values.

13. A medical device for supporting health control, the device comprising the data management unit according to claim 1.

14. A system comprising:
   the medical device according to claim 13; and
   a case configured to carry and secure the medical device, wherein the case comprises at least one flash card containing information related to a use of the medical device.

15. A method for indicating a trend within a plurality of measurement values of a physiological parameter stored in a data storage, wherein each measurement value is stored with an associated time stamp, the method comprising:
   generating, using a measurement unit, measurement values of a physiological parameter in response to a trigger signal from a slot detecting a biological sample of a user;
   automatically generating, using a clock generator, for each of the measurement values of the physiological parameter, an associated time stamp;
   selecting a first group of measurement values and a second group of measurement values from the plurality of measurement values such that the associated time stamp of each of the measurement values of the first group is in a predefined first time interval and the associated time stamp of each of the measurement values of the second group is in a predefined second time interval, wherein the second time interval is more recent than the first time interval;
   determining that a first count of measurement values in the first group satisfies a first threshold number and that a second count of measurement values in the second group satisfies a second threshold number, and in response:
      calculating a median value from the first group of measurement values;
      calculating a mean value from the second group of measurement values;
      calculating a difference between the mean value and the median value;

determining one of a plurality of different trend categories based at least in part on the calculated difference, causing information about the determined trend category to be transmitted to a user, including causing a display unit to display a visual element that corresponds to the determined trend category, and providing guidance for the user to adjust the user's treatment based on the determined one of the different trend categories, wherein the plurality of different trend categories comprises at least an increasing trend, a steady trend, and a decreasing trend.

16. The method according to claim 15, wherein the first time interval is larger than the second time interval.

17. The method according to claim 15, wherein the mean value is calculated as an arithmetic mean value of the measurement values of the second group.

18. The method according to claim 15, wherein the visual element corresponding to the one of the plurality of different trend categories is presented on the display unit if the calculated difference is within a relative tolerance range of the mean value.

19. The method according to claim 15, wherein the visual element corresponding to the one of the plurality of different trend categories is presented on the display unit if the calculated difference is within an absolute tolerance range.

20. The method according to claim 15, wherein the second time interval encompasses the present day.

21. The method according to claim 15, wherein the first time interval and the second time interval do not overlap.

22. The method according to claim 15, wherein an up arrow is presented on the display unit as the visible element for the increasing trend category, a down arrow is presented on the display unit as the visible element for the decreasing trend category, and a horizontal arrow is presented on the display unit as the visible element for the steady trend category.

23. The method according to claim 15, wherein an associated event tag is stored in the data storage for each measurement value, and the event tag is considered for selection of the first group of measurement values and the second group of measurement values from the plurality of measurement values.

24. A computer program product comprising computer-readable instructions tangibly embodied in a non-transitory computer-readable medium, the instructions executable by one or more processing devices to perform operations for indicating a trend within a plurality of measurement values of a physiological parameter stored in a storage, wherein each measurement value is stored with an associated time stamp, the operations comprising:

generating, using a measurement unit, measurement values of a physiological parameter in response to a trigger signal from a slot detecting a biological sample of a user;

automatically generating, using a clock generator, for each of the measurement values of the physiological parameter, an associated time stamp;

selecting a first group of measurement values and a second group of measurement values from the plurality of measurement values such that the associated time stamp of each of the measurement values of the first group is in a predefined first time interval and the associated time stamp of each of the measurement values of the second group is in a predefined second time interval, wherein the second time interval is more recent than the first time interval;

determining that a first count of measurement values in the first group satisfies a first threshold number and that a second count of measurement values in the second group satisfies a second threshold number, and in response:

calculating a median value from the first group of measurement values;

calculating a mean value from the second group of measurement values;

calculating a difference between the mean value and the median value;

determining one of a plurality of different trend categories based at least in part on the calculated difference, causing information about the determined trend category to be transmitted to a user, including causing a display unit to display a visual element that corresponds to the determined trend category, and providing guidance for the user to adjust the user's treatment based on the determined one of the different trend categories, wherein the plurality of different trend categories comprises at least an increasing trend, a steady trend, and a decreasing trend.

* * * * *